United States Patent
Zhang et al.

(10) Patent No.: US 11,360,006 B2
(45) Date of Patent: Jun. 14, 2022

(54) METHOD FOR SEPARATING MICROPLASTICS FROM ANIMAL EXCREMENT

(71) Applicant: Nanjing University, Nanjing (CN)

(72) Inventors: Yan Zhang, Nanjing (CN); Zehua Yan, Nanjing (CN); Hongqiang Ren, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 153 days.

(21) Appl. No.: 16/935,241

(22) Filed: Jul. 22, 2020

(65) Prior Publication Data
US 2020/0400536 A1 Dec. 24, 2020

Related U.S. Application Data

(63) Continuation-in-part of application No. PCT/CN2019/116644, filed on Nov. 8, 2019.

(30) Foreign Application Priority Data

Jun. 19, 2019 (CN) .......................... 201910531601.8

(51) Int. Cl.
*G01N 1/34* (2006.01)
*B01D 71/16* (2006.01)
(Continued)

(52) U.S. Cl.
CPC .............. *G01N 1/34* (2013.01); *B01D 71/16* (2013.01); *B01D 71/20* (2013.01); *B01D 71/36* (2013.01);
(Continued)

(58) Field of Classification Search
CPC ........ B01D 71/16; B01D 71/20; B01D 71/36; G01N 1/34; G01N 1/4044; G01N 1/4077;
(Continued)

(56) References Cited

FOREIGN PATENT DOCUMENTS

CN 109900886 A * 6/2019

OTHER PUBLICATIONS

Espacenet English Translation of CN 109900886 A (Jun. 18, 2019) (Year: 2019).*

* cited by examiner

*Primary Examiner* — Jennifer Wecker
*Assistant Examiner* — Kathryn Elizabeth Limbaugh
(74) *Attorney, Agent, or Firm* — Matthias Scholl P.C.; Matthias Scholl

(57) ABSTRACT

A method for separating microplastics from an animal feces, the method including: 1) freeze-drying an animal fecal sample; 2) transferring the animal fecal sample dried in 1) into a beaker, adding a Fenton's reagent; stirring a mixture of the animal fecal sample and the Fenton's reagent until no bubbles were produced; constantly adding the Fenton's reagent to the mixture; filtering the mixture through a plurality of cellulose nitrate-cellulose acetate (CN-CA) membranes, and transferring the plurality of CN-CA membranes into a plurality of 500 mL beakers; adding 100 mL of 65% $HNO_3$ to each beaker, placing the each beaker in a water bath firstly at 50° C. for 30 min and then at 70° C. for 15 min; cooling the each beaker in an ice bath, and filtering a solution in the each beaker through a first polytetrafluoroethylene (PTFE) membrane; and 3) transferring the first PTFE membrane into a 500 mL beaker.

9 Claims, 8 Drawing Sheets

(51) Int. Cl.
    *B01D 71/20*         (2006.01)
    *B01D 71/36*         (2006.01)
    *G01N 1/40*          (2006.01)
    *G01N 21/65*         (2006.01)
    *G01N 33/483*       (2006.01)

(52) U.S. Cl.
    CPC .......... *G01N 1/4044* (2013.01); *G01N 1/4077* (2013.01); *G01N 21/65* (2013.01); *G01N 33/4833* (2013.01); *G01N 2001/4088* (2013.01); *G01N 2001/4094* (2013.01)

(58) Field of Classification Search
    CPC ............. G01N 1/28; G01N 2001/4088; G01N 2001/4094; G01N 21/65; G01N 33/4833; G01N 15/00; G01N 15/14
    See application file for complete search history.

METHOD FOR SEPARATING MICROPLASTICS FROM ANIMAL EXCREMENT

CROSS-REFERENCE TO RELATED APPLICATIONS

This application is a continuation-in-part of International Patent Application No. PCT/CN2019/116644 with an international filing date of Nov. 8, 2019, designating the United States, now pending, and further claims foreign priority benefits to Chinese Patent Application No. 201910531601.8 filed Jun. 19, 2019. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to the field of environmental health risk assessment, and more particularly, to a method for separating microplastics from an animal feces. The method can accurately detect the type and abundance of microplastics in the animal feces, which provides technical and data support for the research of the accumulation and excretion of microplastics in and out of the body.

Microplastics are any type of plastic fragment that is less than 5 mm in length and are unfriendly to the environment.

Conventionally, the microplastics are extracted from biological tissues and sludges. Specifically, a biological or sludge sample is directly digested by a strong acid or a strong base, and followed by density fractionation, the microplastics are acquired. However, the density fractionation is not suitable for separating the microplastics from animal feces because the digested organic matters tend to cover the surface of the microplastics. The strong acid or strong base does harm to the microplastics.

SUMMARY

The disclosure provides a method for separating microplastics from an animal feces, the method comprising:
(1) freeze-drying an animal fecal sample, and collecting N g of the animal fecal sample dried;
(2) transferring the animal fecal sample dried in 1) into a beaker, adding a Fenton's reagent comprising 20 g/L of $FeSO_4.7H_2O$ and 30% hydrogen peroxide solution ($H_2O_2$), with a volume ratio thereof being 1:2.5; stirring a mixture of the animal fecal sample and the Fenton's reagent until no bubbles are produced; constantly adding the Fenton's reagent to the mixture, in each addition, 30% $H_2O_2$ is no more than 50 mL, and controlling the temperature of the mixture below 40° C.; filtering the mixture through a plurality of cellulose nitrate-cellulose acetate (CN-CA) membranes, and transferring the plurality of CN-CA membranes into a plurality of 500 mL beakers with each beaker having no more than 3 CN-CA membranes; adding 100 mL of 65% $HNO_3$ to each beaker, placing the each beaker in a water bath firstly at 50° C. for 30 min and then at 70° C. for 15 min; cooling the each beaker in an ice bath, and filtering a solution in the each beaker through a first polytetrafluoroethylene (PTFE) membrane; and
(3) transferring the first PTFE membrane obtained in 2) into a 500 mL beaker, adding 200 mL of absolute ethanol to the beaker; ultrasonically treating a mixture of the first PTFE membrane and absolute ethanol; washing the first PTFE membrane with absolute ethanol three times, removing the first PTFE membrane out of the beaker, and filtering a solution in the beaker through a second PTFE membrane; drying a retentate on the second PTFE membrane and microscopically examining the retentate by using micro-Raman spectrometer to obtain a Raman spectrum, identifying microplastic particles from the retentate.

In 1), N is in the range of 1-5.

In 2), the 20 g/L of $FeSO_4.7H_2O$ is prepared by dissolving 10 g of $FeSO_4.7H_2O$ in 500 mL of distilled water, and a pH value of the 20 g/L of $FeSO_4.7H_2O$ is adjusted to 3 by concentrated sulfuric acid.

In 2), the total addition volume of the 30% $H_2O_2$ is N×100 mL, and a volume ratio of the 20 g/L of $FeSO_4.7H_2O$ to the 30% $H_2O_2$ is 1:2.5.

In 2), the total number of the plurality of CN-CA membranes is M=2N+1, where M is an integer, and N is in the range of 1-5.

In 2), the pore diameter of both the CN-CA membranes and the PTFE membranes is 1 μm.

In 3), the mixture of the first PTFE membrane and absolute ethanol is ultrasonically processed for 10-15 min.

In 1), the animal feces are selected from human feces, livestock feces and poultry feces, and at least 3 parallel samples of animal feces are provided.

The extraction method of the disclosure can quickly and efficiently extract the microplastics from animal feces, with high fidelity and minimized impact on the microplastics. The method can also detect the type and abundance of microplastics in feces of a certain weight. The method employs the Fenton's agent to digest the easily digestible organic matter in the feces, then digest the CN-CA membranes and the remaining organic matter by $HNO_3$ in a 50° C. water bath, and further digest the difficulty digestible organic matter by $HNO_3$ at a 70° C. water bath. After digestion of the feces, absolute ethanol is used to dissolve the remaining organic material covering the surface of the microplastic, thereby improving the efficiency of identifying microplastics by Raman spectroscopy.

DETAILED DESCRIPTION OF THE EMBODIMENTS

Figure 1:
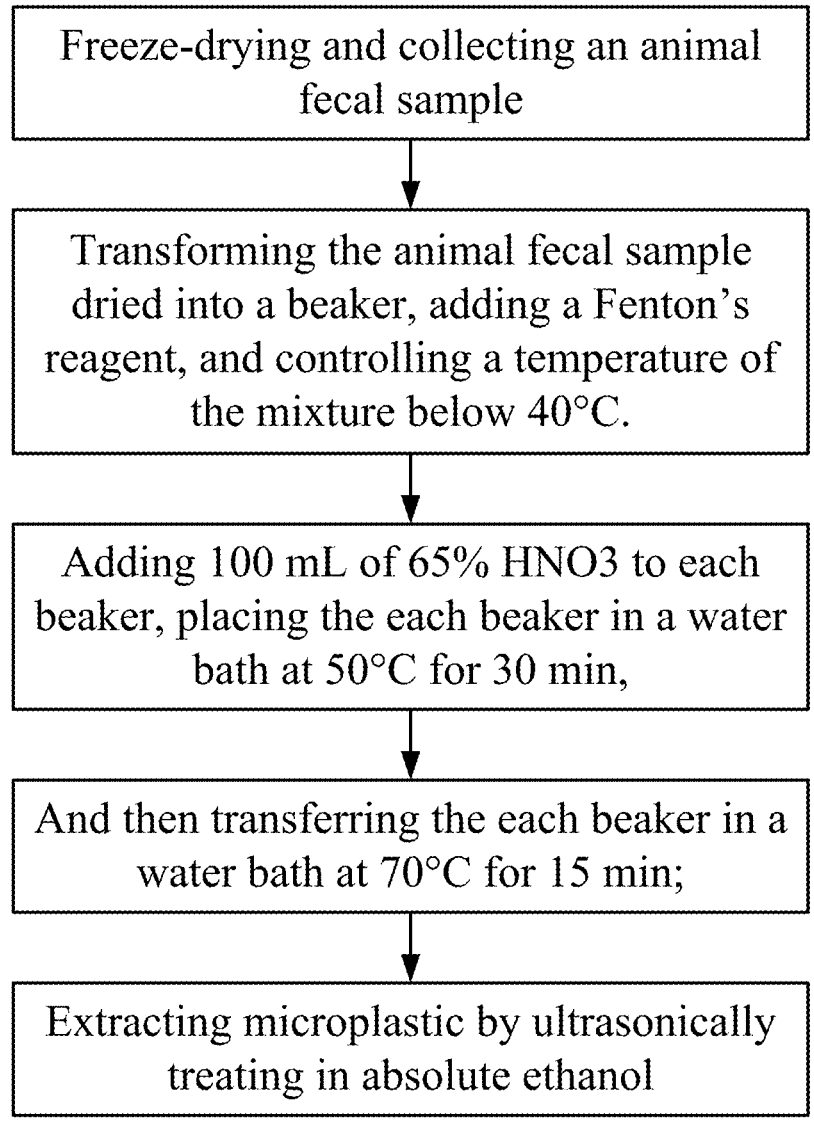
FIG. 1 is a process flow of a method for separating microplastics from animal feces according to one embodiment of the disclosure.

To further illustrate, embodiments detailing a method for separating microplastics from an animal feces are described below. It should be noted that the following embodiments are intended to describe and not to limit the disclosure.

The disclosure provides a method for separating microplastics from an animal feces. The extraction method mainly comprises: 1) freeze-drying a fecal sample in a freeze-dryer; 2) adding a digestion reagent to completely digest the fecal sample, and 3) separating the microplastics by vacuum filtration and ultrasonic cleaning. The disclosure can quickly and efficiently extract the microplastics in feces from human, livestock or poultry, with the minimized impact on microplastics. The method can also detect accurately the type and abundance of microplastics in the animal feces of a certain weight, which provides strong technical and data support to research the accumulation and excretion of microplastics in and out of the body.

Specifically, the method comprises:

(1) freeze-drying an animal fecal sample, and collecting N g of the animal fecal sample dried;

(2) transferring the animal fecal sample dried in 1) into a beaker, adding a Fenton's reagent comprising 20 g/L of $FeSO_4.7H_2O$ and 30% hydrogen peroxide solution ($H_2O_2$), with a volume ratio thereof being 1:2.5; stirring a mixture of the animal fecal sample and the Fenton's reagent until no bubbles are produced; constantly adding the Fenton's reagent to the mixture, in each addition, 30% $H_2O_2$ is no more than 50 mL, and controlling the temperature of the mixture below 40° C.; filtering the mixture through a plurality of cellulose nitrate-cellulose acetate (CN-CA) membranes, and transferring the plurality of CN-CA membranes into a plurality of 500 mL beakers with each beaker having no more than 3 CN-CA membranes; adding 100 mL of 65% $HNO_3$ to each beaker, placing the each beaker in a water bath firstly at 50° C. for 30 min and then at 70° C. for 15 min; cooling the each beaker in an ice bath, and filtering a solution in the each beaker through a first polytetrafluoroethylene (PTFE) membrane; and (3) transferring the first PTFE membrane obtained in 2) into a 500 mL beaker, adding 200 mL of absolute ethanol to the beaker; ultrasonically treating a mixture of the first PTFE membrane and absolute ethanol; washing the first PTFE membrane with absolute ethanol three times, removing the first PTFE membrane out of the beaker, and filtering a solution in the beaker through a second PTFE membrane; drying a retentate on the second PTFE membrane and microscopically examining the retentate by using micro-Raman spectrometer to obtain a Raman spectrum, identifying microplastic particles from the retentate.

In 1), N is in the range of 1-5.

In 2), the 20 g/L of $FeSO_4.7H_2O$ is prepared by dissolving 10 g of $FeSO_4.7H_2O$ in 500 mL of distilled water, and a pH value of the 20 g/L of $FeSO_4.7H_2O$ is adjusted to 3 by concentrated sulfuric acid.

In 2), the total addition volume of the 30% $H_2O_2$ is N×100 mL, and a volume ratio of the 20 g/L of $FeSO_4.7H_2O$ to the 30% $H_2O_2$ is 1:2.5.

In 2), the total number of the plurality of CN-CA membranes is M=2N+1, where M is an integer, and N is in the range of 1-5.

In 2), the pore diameter of both the CN-CA membranes and the PTFE membranes is 1 μm.

In 3), the mixture of the first PTFE membrane and absolute ethanol is ultrasonically processed for 10-15 min.

In 1), the animal feces are selected from human feces, livestock feces and poultry feces, and at least 3 parallel samples of animal feces are provided.

Example 1

(1) Freeze-drying of sample: the human feces were freeze-dried in a freeze-dryer, and 5 g of dried sample was collected. Three dried samples were prepared.

(2) Sample digestion: the freeze-dried fecal samples in 1) was transferred to a 2 L beaker, followed by addition of Fenton's reagent comprising 20 mL of 20 g/L of $FeSO_4.7H_2O$ (10 g of $FeSO_4.7H_2O$ was dissolved in 500 mL of distilled water, pH=3) and 50 mL of 30% hydrogen peroxide solution ($H_2O_2$). The mixture was stirred by a magnetic stirrer until no bubbles were produced, and the Fenton's reagent comprising no more than 50 mL of 30% $H_2O_2$ was constantly added until 200 mL of 30% $H_2O_2$ was added. The reaction temperature was kept below 40° C. The remaining organic matter was filtered through CN-CA membranes by using a water circulating vacuum pump, where the number of the CN-CA membranes was M=10. The CN-CA membranes were transferred to other 500 mL beakers, with each beaker having equal to or less than 3 sheets of membranes. 100 mL of 65% $HNO_3$ was added to each of the beakers, and the mixture was digested in a water bath firstly at 50° C. for 30 min and then at 70° C. for 15 min, and then cooled in an ice bath. The solution was filtered through the PTFE membranes by using the water circulating vacuum pump.

(3) Sample extraction: the PTFE membranes from 2) were transferred to a 500 mL beaker, followed by addition of 200 mL of absolute ethanol. The PTFE membranes were ultrasonically cleaned at 100 kHz for 10-15 min, and washed with absolute ethanol three times. The PTFE membranes were collected, and the remaining solution in the beakers were filtered through the PTFE membranes by using the water circulating vacuum pump. The retentate on the PTFE membranes were dried and weighed.

Figure 2:
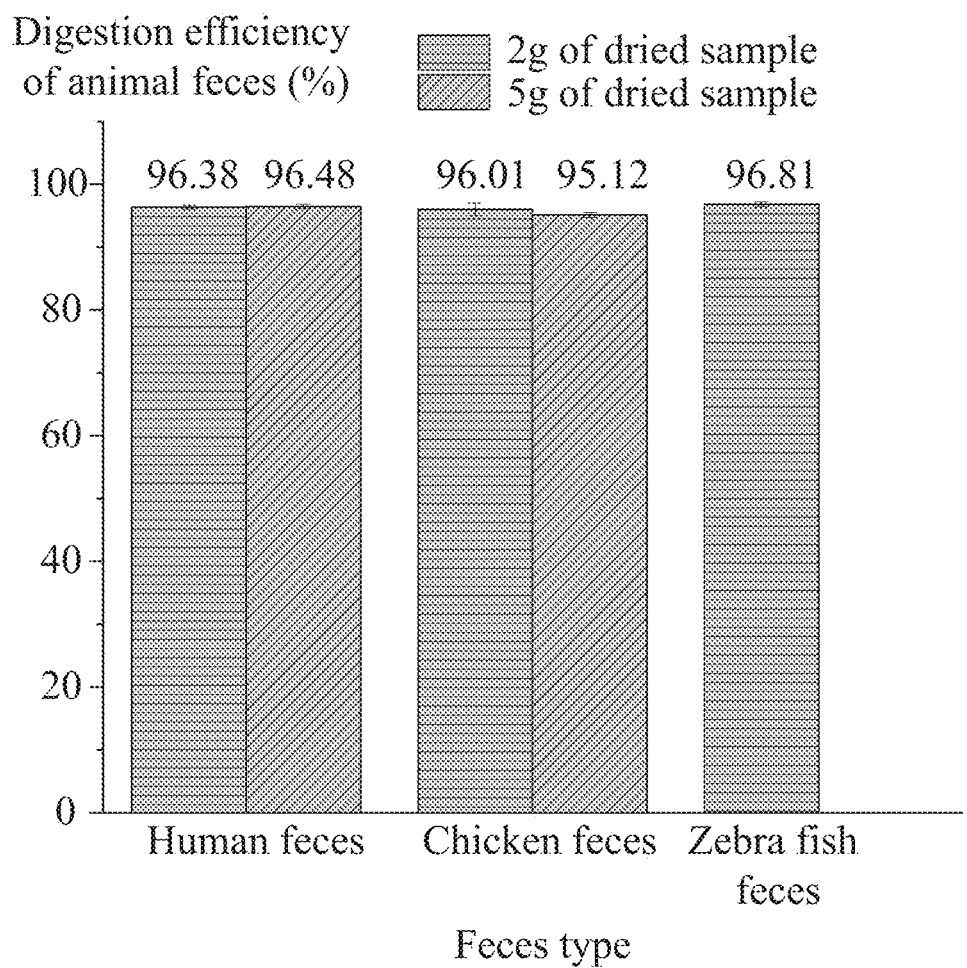
FIG. 2 is a diagram of a digestion efficiency of animal feces according to one embodiment of the disclosure.

The PTFE membranes were dried and weighed. FIG. 2 is a diagram of the digestion efficiency of the fecal samples.

Example 2

(1) Freeze-drying of sample: the human feces were freeze-dried in a freeze-dryer, and 2 g of dried sample was collected. Three dried samples were prepared.

(2) Sample digestion: the freeze-dried fecal samples in 1) was transferred to a 2 L beaker, followed by addition of Fenton's reagent comprising 20 mL of 20 g/L of $FeSO_4.7H_2O$ (10 g of $FeSO_4.7H_2O$ was dissolved in 500 mL of distilled water, pH=3) and 50 mL of 30% hydrogen peroxide solution ($H_2O_2$). The mixture was stirred by a magnetic stirrer until no bubbles were produced, and the Fenton's reagent comprising no more than 50 mL of 30% $H_2O_2$ was constantly added until 200 mL of 30% $H_2O_2$ was added. The reaction temperature was kept below 40° C. The remaining organic matter was filtered through CN-CA membranes by using a water circulating vacuum pump, where the number of the CN-CA membranes was M=5. The CN-CA membranes were transferred to other 500 mL beakers, with each beaker having equal to or less than 3 sheets of membranes. 100 mL of 65% $HNO_3$ was added to each of the beakers, and the mixture was digested in a water bath firstly at 50° C. for 30 min and then at 70° C. for 15 min, and then cooled in an ice bath. The solution was filtered through the PTFE membranes by using the water circulating vacuum pump.

(3) Sample extraction: the PTFE membranes from 2) were transferred to a 500 mL beaker, followed by addition of 200 mL of absolute ethanol. The PTFE membranes were ultrasonically cleaned at 100 kHz for 10-15 min, and washed with absolute ethanol three times. The PTFE membranes were collected, and the remaining solution in the beakers were filtered through the PTFE membranes by using the water circulating vacuum pump. The retentate on the PTFE membranes were dried and weighed.

The PTFE membranes were dried and weighed. FIG. 2 is a diagram of the digestion efficiency of the fecal samples.

Example 3

(1) Freeze-drying of sample: the chicken manure was freeze-dried in a freeze-dryer, and 5 g of dried sample was collected. Three dried samples were prepared.

(2) Sample digestion: the freeze-dried fecal samples in 1) was transferred to a 2 L beaker, followed by addition of Fenton's reagent comprising 20 mL of 20 g/L of $FeSO_4.7H_2O$ (10 g of $FeSO_4.7H_2O$ was dissolved in 500 mL of distilled water, pH=3) and 50 mL of 30% hydrogen peroxide solution ($H_2O_2$). The mixture was stirred by a magnetic stirrer until no bubbles were produced, and the Fenton's reagent comprising no more than 50 mL of 30% $H_2O_2$ was constantly added until 500 mL of 30% $H_2O_2$ was added. The reaction temperature was kept below 40° C. The remaining organic matter was filtered through CN-CA membranes by using a water circulating vacuum pump, where the number of the CN-CA membranes was M=11. The CN-CA membranes were transferred to other 500 mL beakers, with each beaker having equal to or less than 3 sheets of membranes. 100 mL of 65% $HNO_3$ was added to each of the beakers, and the mixture was digested in a water bath firstly at 50° C. for 30 min and then at 70° C. for 15 min, and then cooled in an ice bath. The solution was filtered through the PTFE membranes by using the water circulating vacuum pump.

(3) Sample extraction: the PTFE membranes from 2) were transferred to a 500 mL beaker, followed by addition of 200 mL of absolute ethanol. The PTFE membranes were ultrasonically cleaned at 100 kHz for 10-15 min, and washed with absolute ethanol three times. The PTFE membranes were collected, and the remaining solution in the beakers were filtered through the PTFE membranes by using the water circulating vacuum pump. The retentate on the PTFE membranes were dried and weighed.

The PTFE membranes were dried and weighed. FIG. 2 is a diagram of the digestion efficiency of the fecal samples.

Example 4

(1) Freeze-drying of sample: the chicken manure was freeze-dried in a freeze-dryer, and 2 g of dried sample was collected. Three dried samples were prepared.

(2) Sample digestion: the freeze-dried fecal samples in 1) was transferred to a 2 L beaker, followed by addition of Fenton's reagent comprising 20 mL of 20 g/L of $FeSO_4.7H_2O$ (10 g of $FeSO_4.7H_2O$ was dissolved in 500 mL of distilled water, pH=3) and 50 mL of 30% hydrogen peroxide solution ($H_2O_2$). The mixture was stirred by a magnetic stirrer until no bubbles were produced, and the Fenton's reagent comprising no more than 50 mL of 30% $H_2O_2$ was constantly added until 200 mL of 30% $H_2O_2$ was added. The reaction temperature was kept below 40° C. The remaining organic matter was filtered through CN-CA membranes by using a water circulating vacuum pump, where the number of the CN-CA membranes was M=5. The CN-CA membranes were transferred to other 500 mL beakers, with each beaker having equal to or less than 3 sheets of membranes. 100 mL of 65% $HNO_3$ was added to each of the beakers, and the mixture was digested in a water bath firstly at 50° C. for 30 min and then at 70° C. for 15 min, and then cooled in an ice bath. The solution was filtered through the PTFE membranes by using the water circulating vacuum pump.

(3) Sample extraction: the PTFE membranes from 2) were transferred to a 500 mL beaker, followed by addition of 200 mL of absolute ethanol. The PTFE membranes were ultrasonically cleaned at 100 kHz for 10-15 min, and washed with absolute ethanol three times. The PTFE membranes were collected, and the remaining solution in the beakers were filtered through the PTFE membranes by using the water circulating vacuum pump. The retentate on the PTFE membranes were dried and weighed.

The PTFE membranes were dried and weighed. FIG. 2 is a diagram of the digestion efficiency of the fecal samples.

Example 5

(1) Freeze-drying of sample: the zebrafish manure was freeze-dried in a freeze-dryer, and 2 g of dried sample was collected. Three dried samples were prepared.

(2) Sample digestion: the freeze-dried fecal samples in 1) was transferred to a 2 L beaker, followed by addition of Fenton's reagent comprising 20 g/L of $FeSO_4.7H_2O$ and 30% hydrogen peroxide solution ($H_2O_2$) with a volume ratio of 1:2.5. The mixture was stirred by a magnetic stirrer until no bubbles were produced, and the Fenton's reagent comprising no more than 50 mL of 30% $H_2O_2$ was constantly added until 200 mL of 30% $H_2O_2$ was added. The reaction temperature was kept below 40° C. The remaining organic matter was filtered through CN-CA membranes by using a water circulating vacuum pump, where the number of the CN-CA membranes was M=5. The CN-CA membranes were transferred to other 500 mL beakers, with each beaker having less than 3 sheets of membranes. 100 mL of 65% $HNO_3$ was added to each of the beakers, and the mixture was digested in a water bath firstly at 50° C. for 30 min and then at 70° C. for 15 min, and then cooled in an ice bath. The solution was filtered through the PTFE membranes by using the water circulating vacuum pump. The retentate on the PTFE membranes were dried and weighed.

(3) Sample extraction: the PTFE membranes from 2) were transferred to a 500 mL beaker, followed by addition of 200 mL of absolute ethanol. The PTFE membranes were ultrasonically cleaned at 100 kHz for 10-15 min, and washed with absolute ethanol three times. The PTFE membranes were collected, and the remaining solution in the beakers were filtered through the PTFE membranes by using the water circulating vacuum pump. The retentate on the PTFE membranes were dried and weighed.

The PTFE membranes were dried and weighed. FIG. 2 is a diagram of the digestion efficiency of the fecal samples Example 6

(1) Freeze-drying of sample: the human feces were freeze-dried in a freeze-dryer, and 5 g of dried sample was collected. Three dried samples were prepared. The three dried samples were mixed with 10 PS plastic particles having a particle size of 250 μm, 10 PE plastic particles having a particle size of 150 and 10 PVC plastic particles having a particle size of 75 respectively, in distilled water, and were then freeze-dried.

(2) Sample digestion: the freeze-dried fecal samples in 1) was transferred to a 2 L beaker, followed by addition of Fenton's reagent comprising 20 mL of 20 g/L of $FeSO_4 \cdot 7H_2O$ (10 g of $FeSO_4 \cdot 7H_2O$ was dissolved in 500 mL of distilled water, pH=3) and 50 mL of 30% hydrogen peroxide solution ($H_2O_2$). The mixture was stirred by a magnetic stirrer until no bubbles were produced, and the Fenton's reagent comprising no more than 50 mL of 30% $H_2O_2$ was constantly added until 200 mL of 30% $H_2O_2$ was added. The reaction temperature was kept below 40° C. The remaining organic matter was filtered through CN-CA membranes by using a water circulating vacuum pump, where the number of the CN-CA membranes was M=11. The CN-CA membranes were transferred to other 500 mL beakers, with each beaker having equal to or less than 3 sheets of membranes. 100 mL of 65% $HNO_3$ was added to each of the beakers, and the mixture was digested in a water bath firstly at 50° C. for 30 min and then at 70° C. for 15 min, and then cooled in an ice bath. The solution was filtered through the PTFE membranes by using the water circulating vacuum pump.

(3) Sample extraction: the PTFE membranes from 2) were transferred to a 500 mL beaker, followed by addition of 200 mL of absolute ethanol. The PTFE membranes were ultrasonically cleaned for 10-15 min, and washed with absolute ethanol three times. The PTFE membranes were collected, and the remaining solution in the beakers were filtered through the PTFE membranes by using the water circulating vacuum pump. The retentate on the PTFE membranes were dried and examined. The suspected microplastics were checked by using micro-Raman spectrometer.

Figure 3:
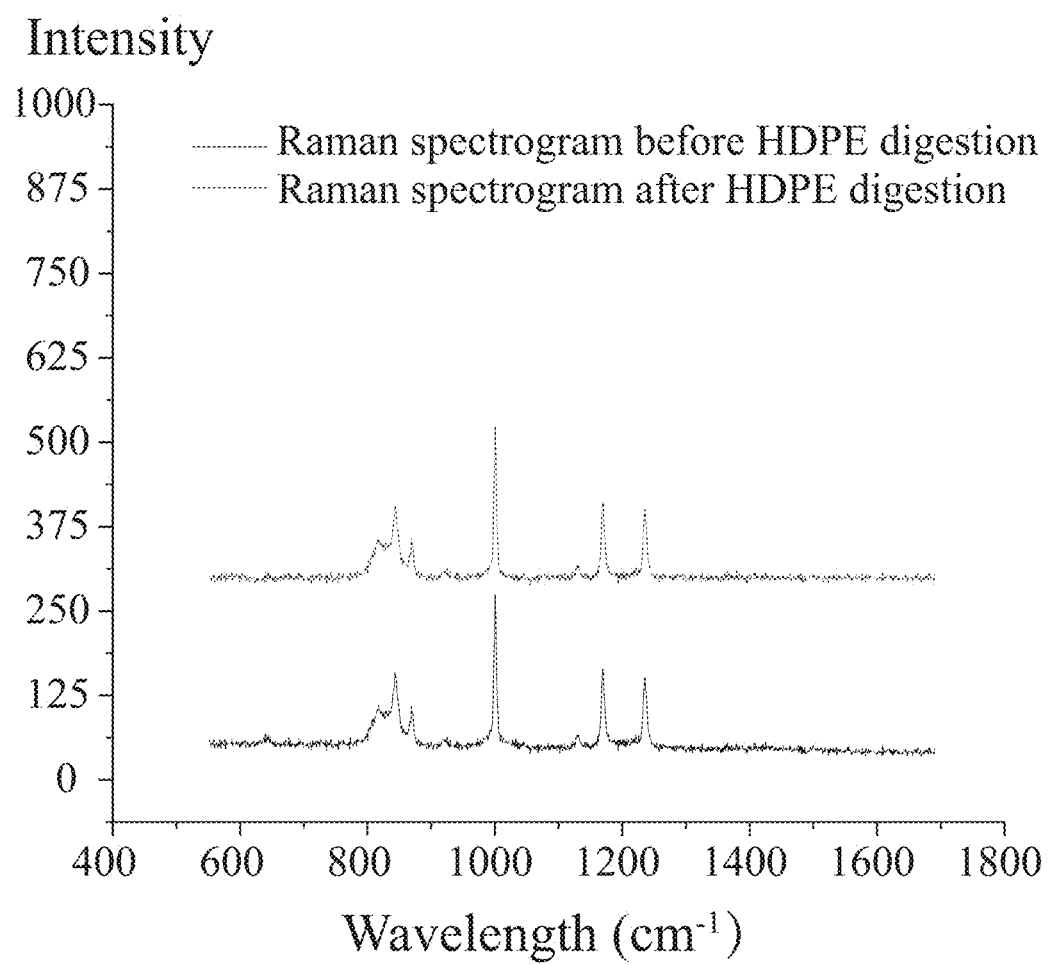
FIG. 3 is a comparison diagram of Raman spectrums of PE plastics prior to and after the digestion of the feces.
Figure 4:
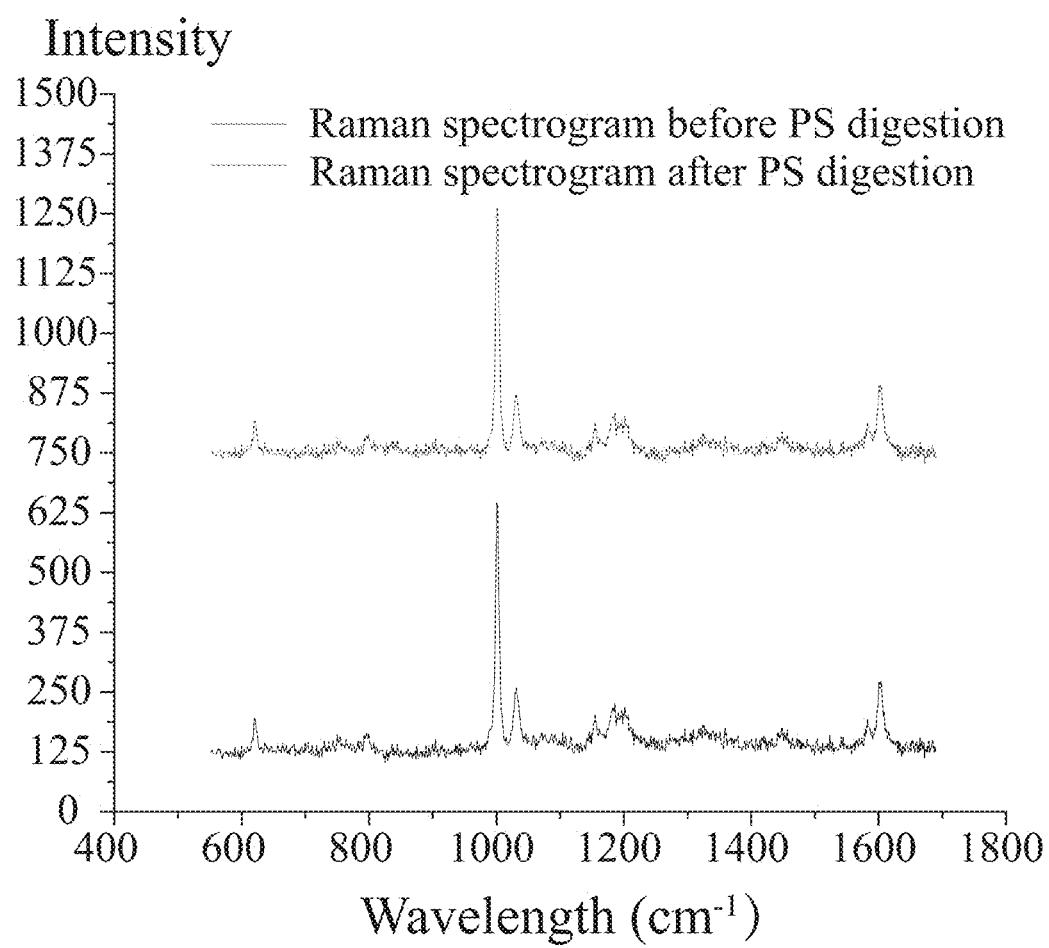
FIG. 4 is a comparison diagram of Raman spectrums of PS plastics prior to and after the digestion of the feces.
Figure 5:
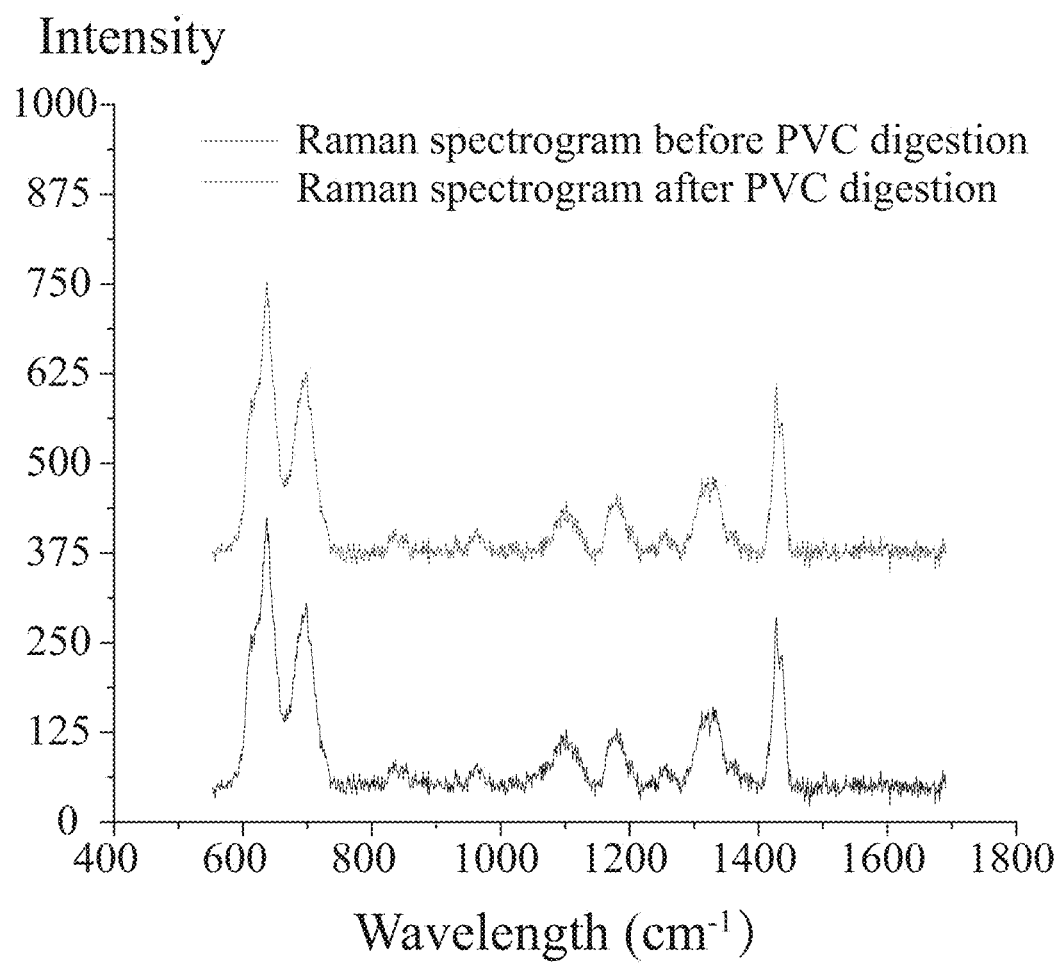
FIG. 5 is a comparison diagram of Raman spectrums of PVC plastics prior to and after the digestion of the feces.
Figure 6:
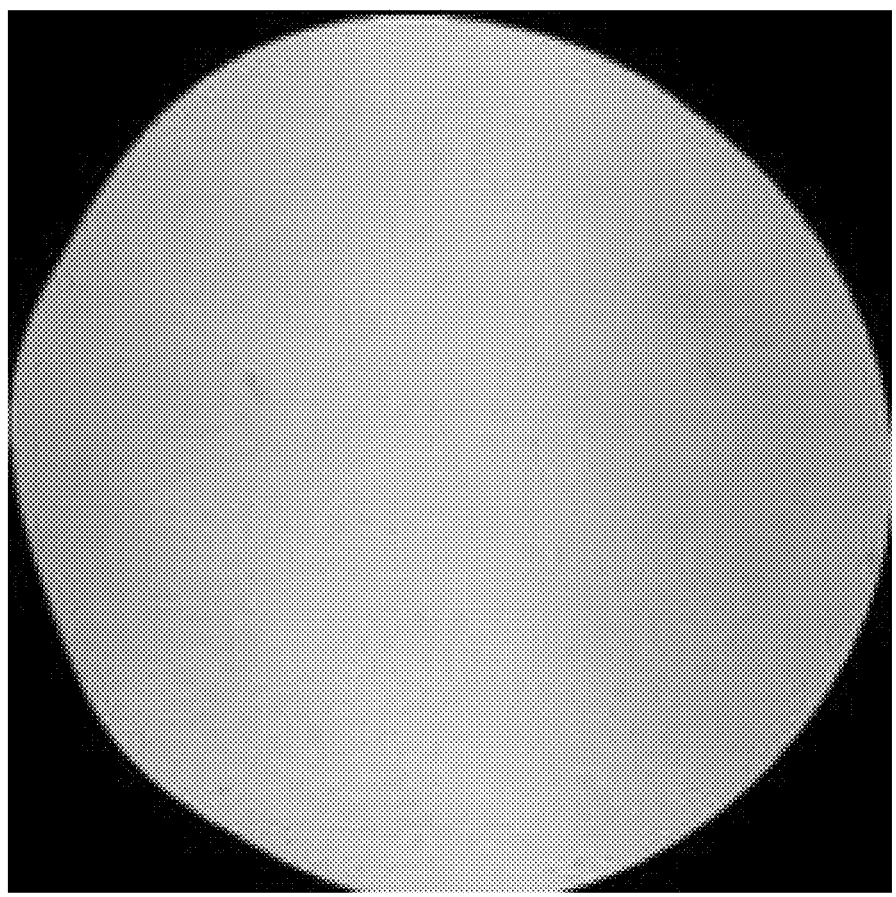
FIG. 6 is a microscopic image of the microplastics extracted by a method for separating microplastics from animal feces according to one embodiment of the disclosure.
Figure 7:
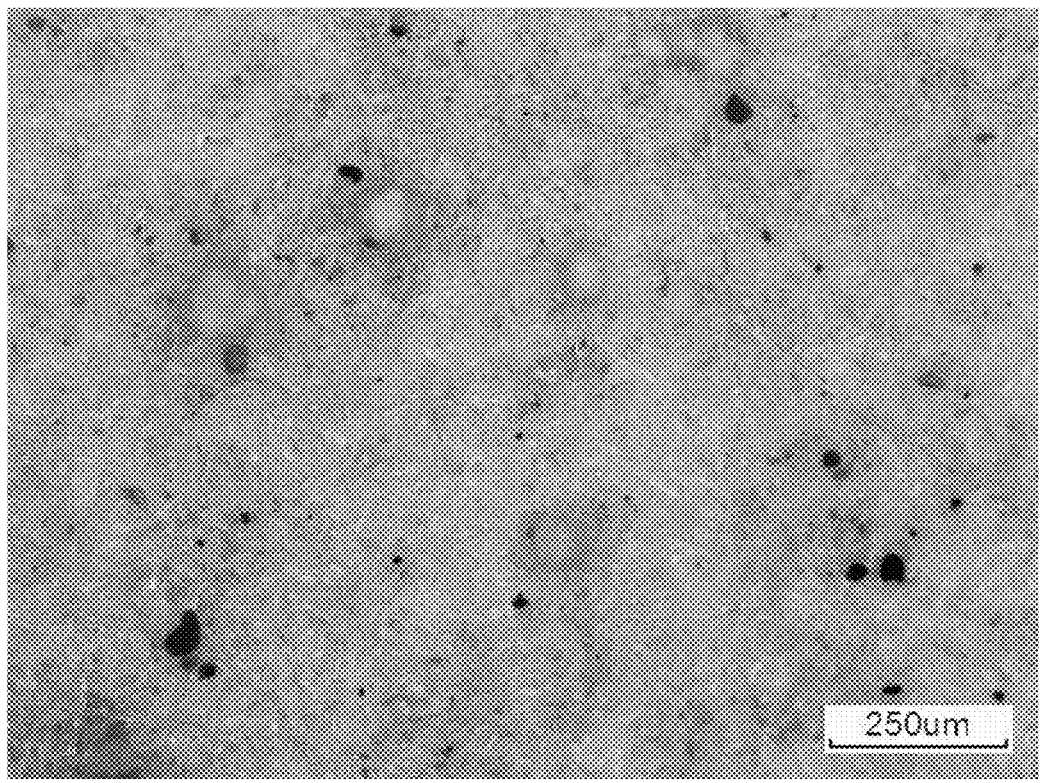
FIG. 7 is an image of organic matter residues on the PTFE membranes after the fecal sample is digested according to one embodiment of the disclosure.
Figure 8:
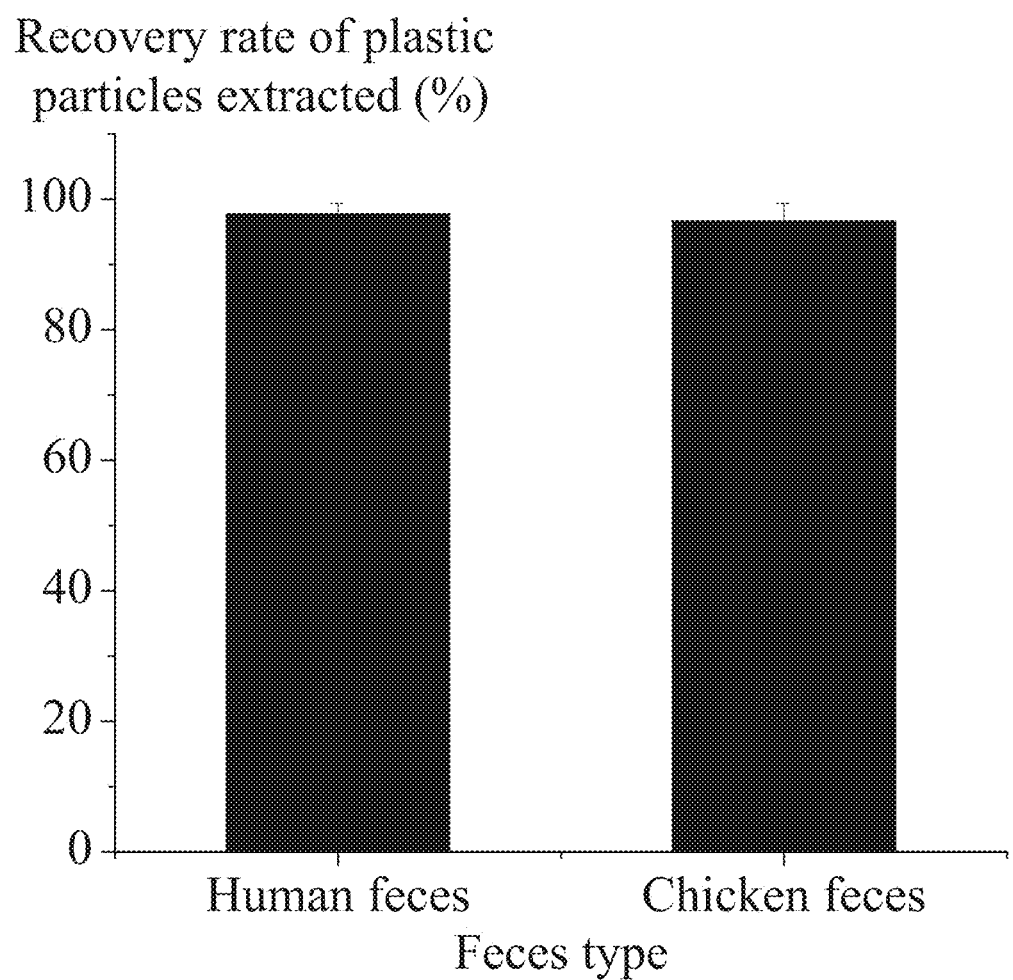
FIG. 8 is a diagram of recovery rate of plastic particles extracted by the method of the disclosure.

The suspected microplastics on the PTFE membranes were checked by using micro-Raman spectrometer. FIGS. 3-4 are diagrams of the digestion efficiency of the fecal samples.

Example 7

(1) Freeze-drying of sample: the chicken manure was freeze-dried in a freeze-dryer, and 5 g of dried sample was collected. Three dried samples were prepared. The three dried samples were mixed with 10 PS plastic particles having a particle size of 250 μm, 10 PE plastic particles having a particle size of 150 μm, and 10 PVC plastic particles having a particle size of 75 μm, respectively, in distilled water, and were then freeze-dried.

(2) Sample digestion: the freeze-dried fecal samples in 1) was transferred to a 2 L beaker, followed by addition of Fenton's reagent comprising 20 mL of 20 g/L of $FeSO_4 \cdot 7H_2O$ (10 g of $FeSO_4 \cdot 7H_2O$ was dissolved in 500 mL of distilled water, pH=3) and 50 mL of 30% hydrogen peroxide solution ($H_2O_2$). The mixture was stirred by a magnetic stirrer until no bubbles were produced, and the Fenton's reagent comprising no more than 50 mL of 30% $H_2O_2$ was constantly added until 200 mL of 30% $H_2O_2$ was added. The reaction temperature was kept below 40° C. The remaining organic matter was filtered through CN-CA membranes by using a water circulating vacuum pump, where the number of the CN-CA membranes was M=11. The CN-CA membranes were transferred to other 500 mL beakers, with each beaker having equal to or less than 3 sheets of membranes. 100 mL of 65% $HNO_3$ was added to each of the beakers, and the mixture was digested in a water bath firstly at 50° C. for 30 min and then at 70° C. for 15 min, and then cooled in an ice bath. The solution was filtered through the PTFE membranes by using the water circulating vacuum pump.

(3) Sample extraction: the PTFE membranes from 2) were transferred to a 500 mL beaker, followed by addition of 200 mL of absolute ethanol. The PTFE membranes were ultrasonically cleaned for 10-15 min, and washed with absolute ethanol three times. The PTFE membranes were collected, and the remaining solution in the beakers were filtered through the PTFE membranes by using the water circulating vacuum pump. The retentate on the PTFE membranes were dried and examined. The suspected microplastics were checked by using micro-Raman spectrometer. The PTFE membranes were dried and weighed.

The suspected microplastics on the PTFE membranes were checked by using micro-Raman spectrometer. FIGS. 3-4 are diagrams of the digestion efficiency of the fecal samples.

It will be obvious to those skilled in the art that changes and modifications may be made, and therefore, the aim in the appended claims is to cover all such changes and modifications.

What is claimed is:

1. A method, comprising:
   1) freeze-drying an animal fecal sample, and collecting N g of the animal fecal sample dried;
   2) transferring the animal fecal sample dried in 1) into a beaker, adding a Fenton's reagent comprising 20 g/L of $FeSO_4 \cdot 7H_2O$ and 30% hydrogen peroxide solution ($H_2O_2$), with a volume ratio of the $FeSO_4 \cdot 7H_2O$ to the 30% $H_2O_2$ being 1:2.5; stirring a mixture of the animal fecal sample and the Fenton's reagent until no bubbles are produced; constantly adding the Fenton's reagent to the mixture, in each addition, 30% $H_2O_2$ is no more than 50 ml, and controlling a temperature of the mixture below 40° C.; filtering the mixture through a plurality of cellulose nitrate-cellulose acetate (CN-CA) membranes, and transferring the plurality of CN-CA membranes into a plurality of 500 mL beakers with each beaker having no more than 3 CN-CA membranes; adding 100 mL of 65% $HNO_3$ to each beaker, placing the each beaker in a water bath firstly at 50° C. for 30 min and then at 70° C. for 15 min; cooling the each beaker in an ice bath, and filtering a solution in the each beaker through a first polytetrafluoroethylene (PTFE) membrane; and
   3) transferring the first PTFE membrane obtained in 2) into a 500 mL beaker, adding 200 mL of absolute ethanol to the beaker; ultrasonically treating a mixture of the first PTFE membrane and absolute ethanol; washing the first PTFE membrane with absolute ethanol three times, removing the first PTFE membrane out of the beaker, and filtering a solution in the beaker through a second PTFE membrane; drying a retentate on the second PTFE membrane and microscopically examining the retentate by using micro-Raman spectrometer to obtain a Raman spectrum, and identifying microplastic particles from the retentate.

2. The method of claim 1, wherein in 1), N is in the range of 1-5.

3. The method of claim 1, wherein in 2), the 20 g/L of $FeSO_4 \cdot 7H_2O$ is prepared by dissolving 10 g of $FeSO_4 \cdot 7H_2O$ in 500 mL of distilled water, and a pH value of the 20 g/L of $FeSO_4 \cdot 7H_2O$ is adjusted to 3 by concentrated sulfuric acid.

4. The method of claim 1, wherein in 2), a total addition volume of the 30% $H_2O_2$ is N×100 mL, and a volume ratio of the 20 g/L of $FeSO_4 \cdot 7H_2O$ to the 30% $H_2O_2$ is 1:2.5.

5. The method of claim 1, wherein in 2), a total number of the plurality of CN-CA membranes is M=2N+1, where M is an integer, and N is in the range of 1-5.

6. The method of claim 1, wherein in 2), a pore diameter of both the CN-CA membranes and the PTFE membranes is 1 μm.

7. The method of claim 1, wherein in 3), the mixture of the first PTFE membrane and absolute ethanol is ultrasonically processed for 10-15 min.

8. The method of claim 1, wherein in 1), the animal feces are selected from human feces, livestock feces and poultry feces.

9. The method of claim 1, wherein in 1), at least 3 parallel samples of animal feces are provided.

\* \* \* \* \*